(12) United States Patent
Perry et al.

(10) Patent No.: US 7,594,422 B2
(45) Date of Patent: Sep. 29, 2009

(54) APPARATUS AND METHOD FOR CALIBRATING A TRACE DETECTION PORTAL

(75) Inventors: Kevin J. Perry, Pelham, NH (US); Michael E. Patterson, Amesbury, MA (US)

(73) Assignee: GE Homeland Protection, Inc., Newark, CA (US)

( * ) Notice: Subject to any disclaimer, the term of this patent is extended or adjusted under 35 U.S.C. 154(b) by 131 days.

(21) Appl. No.: 11/554,160

(22) Filed: Oct. 30, 2006

(65) Prior Publication Data

US 2008/0098794 A1    May 1, 2008

(51) Int. Cl.
G01N 21/93 (2006.01)
G01N 29/30 (2006.01)

(52) U.S. Cl. .................. 73/1.02; 73/1.06; 73/1.07

(58) Field of Classification Search ............... 73/1.02, 73/1.03, 23.3, 23.34, 23.33, 31.01, 31.03, 73/28.01, 28.04, 28.05, 31.02
See application file for complete search history.

(56) References Cited

U.S. PATENT DOCUMENTS

| | | | | |
|---|---|---|---|---|
| 3,290,920 A | * | 12/1966 | Novak | 73/1.03 |
| 3,791,192 A | * | 2/1974 | Butler | 73/1.03 |
| 4,045,997 A | * | 9/1977 | Showalter et al. | 73/23.2 |
| 4,202,200 A | * | 5/1980 | Ellson | 73/31.05 |
| 4,331,862 A | * | 5/1982 | Ryan | 377/29 |
| 4,896,547 A | * | 1/1990 | Arney et al. | 73/863.81 |
| 5,493,890 A | * | 2/1996 | Dussault et al. | 73/1.06 |
| 5,502,998 A | * | 4/1996 | Miller et al. | 73/1.06 |
| 5,604,295 A | * | 2/1997 | Robinson | 73/1.03 |
| 5,753,832 A | * | 5/1998 | Bromberg et al. | 73/864.81 |
| 5,762,475 A | * | 6/1998 | Maddock et al. | 417/29 |
| 5,915,268 A | * | 6/1999 | Linker et al. | 73/23.2 |
| 5,918,254 A | * | 6/1999 | Bottiger et al. | 73/1.06 |
| 6,044,688 A | * | 4/2000 | Dilger | 73/1.05 |
| 6,073,476 A | * | 6/2000 | Reents | 73/1.06 |
| 6,073,499 A | * | 6/2000 | Settles | 73/864.81 |
| 6,334,365 B1 | * | 1/2002 | Linker et al. | 73/864.81 |
| 6,408,674 B1 | * | 6/2002 | Dilger | 73/1.02 |
| 6,627,444 B1 | * | 9/2003 | Goledzinowski et al. | 436/8 |
| 6,642,513 B1 | | 11/2003 | Jenkins et al. | |
| 6,694,796 B2 | * | 2/2004 | Juneau et al. | 73/1.03 |

(Continued)

OTHER PUBLICATIONS

Dr. John E. Parmeter, Dr. Gary A. Eiceman and Jaime E. Rodriguez, "Trace Detection of Narcotics Using a Preconcentrator/Ion Mobility Spectrometer System", NIJ Report 602-00, National Institute of Justice, Washington D.C. Law Enforcement and Corrections Standards and Testing Program, Apr. 2001.

(Continued)

*Primary Examiner*—David A. Rogers
(74) *Attorney, Agent, or Firm*—Global Patent Operation (57) ABSTRACT

Embodiments of the invention provide novel, industrially applicable, and non-obvious apparatus and methods for automatically, routinely, and accurately calibrating a trace detection portal. Embodiments of the apparatus include a calibrant container; a substance (or substances) uniquely identifiable by a trace detection portal as a calibrant; unique placement of the calibrant container's outlet relative to a substance collection port of a sample collection chamber; and/or computer executable instructions that, when executed by a computer processor, cause a consistent release of a measured amount of calibrant into the sample collection chamber upon command and/or at pre-determined time intervals.

9 Claims, 6 Drawing Sheets

U.S. PATENT DOCUMENTS

| | | | |
|---|---|---|---|
| 6,708,572 B2 | 3/2004 | Jenkins et al. | |
| 6,790,249 B2* | 9/2004 | Davies | 55/340 |
| 6,815,670 B2 | 11/2004 | Jenkins et al. | |
| 6,840,122 B1 | 1/2005 | Jenkins et al. | |
| 6,918,281 B2* | 7/2005 | Sussman et al. | 73/1.06 |
| 6,969,357 B1* | 11/2005 | Colman et al. | 600/529 |
| 7,141,786 B2* | 11/2006 | McGann et al. | 250/287 |
| 7,168,287 B2* | 1/2007 | Rolff | 73/1.05 |
| 7,180,441 B2* | 2/2007 | Rowe et al. | 342/22 |
| 7,343,782 B2* | 3/2008 | Damer et al. | 73/31.03 |
| 7,357,043 B2* | 4/2008 | Cumming et al. | 73/864.33 |
| 2003/0029221 A1* | 2/2003 | Juneau et al. | 73/1.02 |
| 2003/0085348 A1* | 5/2003 | Megerle | 250/287 |
| 2003/0145644 A1* | 8/2003 | Rabbett et al. | 73/1.06 |
| 2003/0195396 A1* | 10/2003 | Scarantino et al. | 600/300 |
| 2003/0216660 A1* | 11/2003 | Ben-Oren et al. | 600/532 |
| 2005/0120776 A1 | 6/2005 | Jenkins et al. | |
| 2005/0262924 A1* | 12/2005 | Wood et al. | 73/31.05 |
| 2006/0118416 A1* | 6/2006 | Liu et al. | 204/431 |
| 2006/0195749 A1* | 8/2006 | Cohen et al. | 714/742 |
| 2006/0266098 A1* | 11/2006 | Eickhoff et al. | 73/1.06 |
| 2007/0045128 A1* | 3/2007 | Krafthefer et al. | 205/778.5 |
| 2007/0076101 A1* | 4/2007 | Baer | 348/222.1 |
| 2007/0114386 A1* | 5/2007 | Fischer et al. | 250/288 |
| 2008/0156071 A1* | 7/2008 | Tobias | 73/23.2 |
| 2009/0036758 A1* | 2/2009 | Brauker et al. | 600/309 |
| 2009/0043542 A1* | 2/2009 | Brauker et al. | 702/189 |

OTHER PUBLICATIONS

West African Aviation, Aviation Maintenance & Security Consultants, "Trace Detection", http://www.westafricanaviation.ndo.co.uk/tracedetection.htm, Copyright 2003, West African Aviation.

Various Committee Members, "Opportunites to Improve Airport Passenger Screening with Mass Spectrometry (2004)", http://www.nap.edu/openbook/030909240X/html/1.html.

* cited by examiner

APPARATUS AND METHOD FOR CALIBRATING A TRACE DETECTION PORTAL

BACKGROUND

1. Field of the Invention

The field of the invention relates to threat detection systems generally and, more particularly, to an apparatus and method for calibrating a trace detection portal.

2. Description of Related Art

Extant threat detection systems check persons and objects for traces of substances of interest, such as narcotics and explosives. Such systems operate on the basis that trace amounts of substances of interest tend to be transferred to the body of a person who handles them, and from the person's body to any article the person's body may touch. Attempts have been made to test persons without physically touching them, but articles such as suitcases and handbags are tested by swiping them with a small piece of material that is then inserted into a known type of threat detection apparatus, which tests for the presence of the substance(s) of interest.

A trace detection portal is a known type of threat detection system into and/or through which a person can walk. U.S. Pat. No. 6,073,499 (the "'499 patent") illustrates a known type of trace detection portal. A trace detection portal, such as the one described in the '499 patent, operates based on the principle that a person's body heats the boundary of air surrounding it, and that the heated air, being less dense than ambient air further away from the body, flows upwardly to create a thermal plume about the body. The rising thermal plume entrains particles comprising a substance of interest present on the person's body and carries them up and away from the body. A fan or other airflow generator positioned in a portion of the trace detection portal above the person operates at a speed that approximates the airflow rate of the rising thermal plume. The fan thus directs the thermal plume to a detector without drawing significant volumes of ambient air into the detector. Consequently, a significant concentration of particles comprising the substance of interest is created.

Some types of trace detection portals route the thermal plume directly to a detector for analysis. Other types first route the thermal plume through a trap that collects particles of interest from the thermal plume. The trap is then inserted within a desorber. Within the desorber, the trap is heated rapidly to temperatures of about 200 degrees Celsius to desorb and volatize the trapped particles comprising the substance of interest collected from the thermal plume. Clean air is injected into the desorber at a low rate and suction is applied to draw the clean air and the particles on the trap into the detector. The detector then detects and identifies the presence of the particles comprising the substance of interest. The trap will remain in the desorber until it is time for the next sample collection. The trap is then removed from the desorber, and repositioned across the airflow inlet at the upper portion of the sample collection chamber and rapidly cooled in preparation for the next sample collection. U.S. Patent Application Publication No.: 2004/0131503 illustrates such a known type of desorber and trap.

Calibrating a trace detection portal to accurately and consistently test for particles comprising a substance of interest is difficult, and typically involves misting differing amounts of a calibrant into the trace detection portal's sample collection chamber by hand. For example, calibrant can be delivered into the portal detection chamber using a hand-held container such as a pistol-grip sprayer, aerosol spray can, nasal spay bottle, etc. Delivering an effluence of calibrant into the portal detection chamber in this manner is imprecise for several reasons. First, the amounts of calibrant released will differ from person to person depending on how long each person actuates the hand-held container. Second, if the calibrant is released too far from the upper portion of the detection chamber, ambient airflow turbulence will reduce the concentration too much for calibration purposes. Other challenges include ensuring a trace detection portal is calibrated on a routine basis, for example, at the beginning of each shift, which may be once every eight hours of usage that the trace detection portal is used. Non-calibration can create regular periods during which the portal cannot be used. Such periods decrease the trace detection portal's throughput.

Long-felt needs thus exist for: an apparatus and method that can calibrate a trace detection portal automatically, simply, and accurately; an automatic and accurate calibration apparatus that can be easily retrofitted to existing trace portal detection systems; and a calibration apparatus and method for consistently dispersing a predetermined amount of calibrant into a sample collection chamber at a predetermined distance from a calibrant collection area of the trace detection portal.

SUMMARY OF THE INVENTION

Embodiments of the invention disclosed herein overcome the disadvantages associated with the related art and meet the needs discussed above by providing novel, industrially applicable, and non-obvious apparatus and methods for automatically, simply, and accurately calibrating a trace detection portal. Embodiments of the apparatus include a calibrant container; a substance (or substances) uniquely identifiable by a trace detection portal as a calibrant; unique placement of the calibrant container's outlet relative to a substance collection port of a sample collection chamber; and/or computer executable instructions that, when executed by a computer processor, cause a consistent, repeatable release of a predetermined amount of calibrant into the sample collection chamber upon command and/or at pre-determined time intervals.

Newly manufactured or retrofitted trace detection portals comprising an embodiment of the claimed calibration apparatus and/or using an embodiment of the claimed calibration method may be installed in airports, courthouses, schools, military installations, and any other government, commercial, industrial, or private venue where it is desired to detect threats posed by various types of explosives and/or other substances.

A technical effect afforded by an embodiment of the invention is the output from a component of the trace detection portal of a signal that causes calibrant to be expelled from the calibrant container and into a trace detection portal's sample collection chamber. Another technical effect afforded by an embodiment of the invention is the output from a component of the trace detection portal of a signal that causes the trace detection portal's detector to perform a calibration routine upon detecting and uniquely identifying a substance of interest as a calibrant. Yet another technical effect afforded by an embodiment of the invention is the output from a component of the trace detection portal of a signal that causes a display panel and/or other communication means to indicate the trace detection portal is ready to process a person.

Broadly, an embodiment of the invention includes an apparatus for calibrating a trace detection portal. The apparatus may include a calibrant container having an outlet configured to couple with a sample collection chamber of the trace detection portal. Additional components that may be included in the apparatus described above include means for releasably containing a calibrant, and means for coupling the means for releasably containing a calibrant with a sample collection chamber of the trace detection portal. Means for initiating a release of a predetermined amount of the calibrant into the sample collection chamber, and means for automatically self-calibrating one or more of its components upon detecting and uniquely identifying the calibrant may also be components of the above-described apparatus for calibrating a trace detection portal.

Broadly, another embodiment of the invention provides a method for calibrating a trace detection portal. The method may include the step of providing a calibrant container having an outlet, and the step of releasably storing a calibrant within the calibrant container. The calibrant is a substance the trace detection portal is configured to detect and uniquely identify, and which (upon detection and identification by the trace detection portal) causes one or more components of the trace detection portal to automatically self-calibrate. Self-calibration of a trace detection portal component may include automatically performing one or more steps designed to improve and/or restore the component's operation and/or sensing accuracy.

Additional method steps that may be included as part of the method described above, include the step of receiving a signal from a control means coupled with the trace detection portal; and the step of releasing a predetermined amount of a substance from a calibrant container into the sample collection chamber in response to the signal received from the control means. Other steps may include detecting, analyzing, and identifying the substance. Yet another step may include automatically initiating a self-calibration of one or more components of the trace detection portal upon identifying the substance as a calibrant.

BRIEF DESCRIPTION OF THE DRAWINGS

The above and other aspects of the various embodiments of the claimed invention will become more apparent when the following detailed description is considered together with the accompanying drawings in which:

DETAILED DESCRIPTION OF THE INVENTION

Reference is made herein to the accompanying drawings briefly described above, which show by way of illustration various embodiments of the claimed invention. Persons of ordinary skill in the above-referenced technological field will recognize that other embodiments may be utilized, and that structural, electrical, and procedural changes may be made without departing from the scope of the claimed invention. As used throughout all of the specification, figures, and claims, the singular (illustratively, "substance") includes the plural (illustratively, "substances"), and the plural includes the singular.

Figure 1:
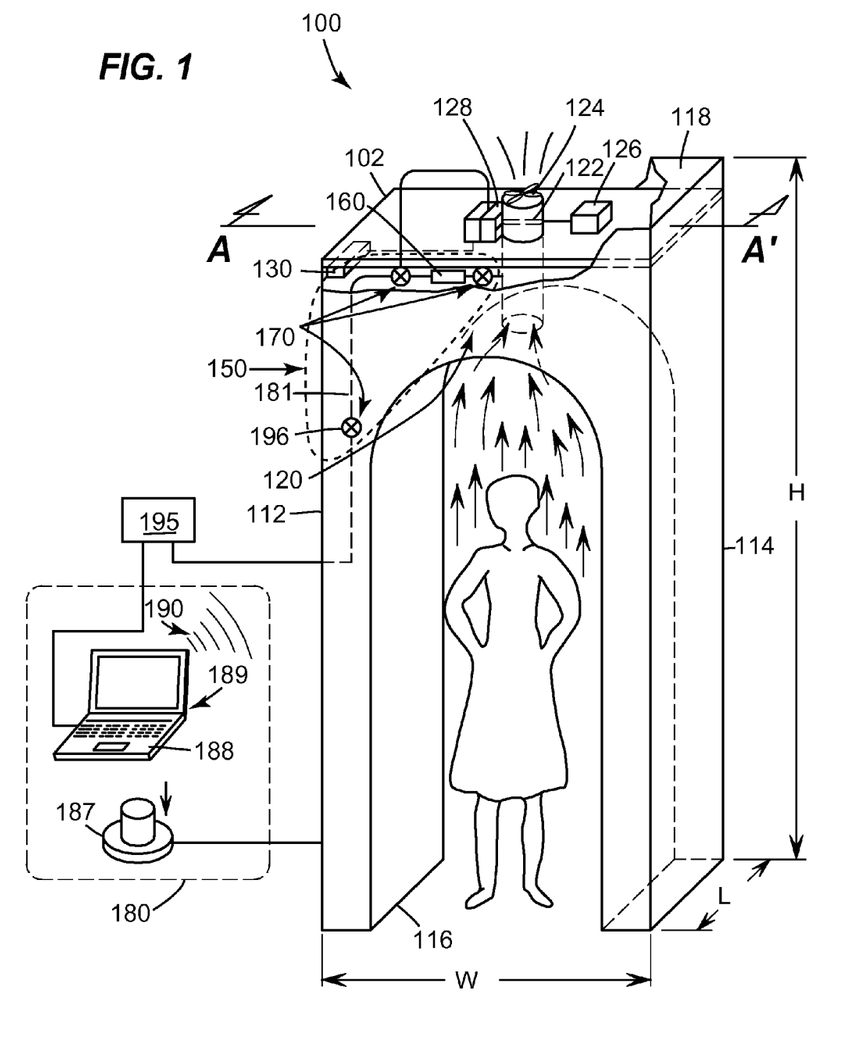
FIG. 1 is a front, perspective, cut-away view of a trace detection portal fitted or retrofitted to include an embodiment of a calibration apparatus.
Figure 2:
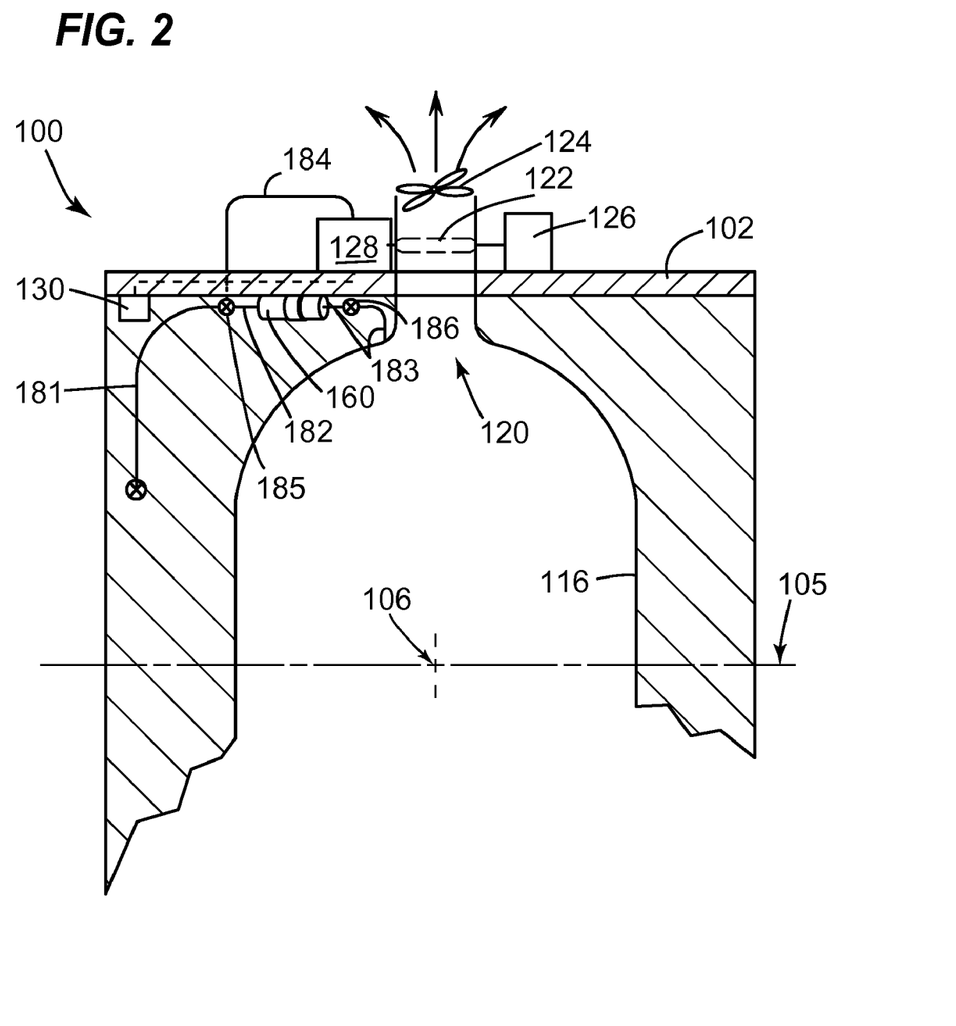
FIG. 2 is an enlarged, cross-sectional view of an upper portion of the trace detection portal of FIG. 1 more clearly depicting an embodiment of the calibration apparatus.

FIG. 1 is a front, perspective, cut-away view of an exemplary trace detection portal 100 originally fitted (or retrofitted) with one or more components of an embodiment of a calibration apparatus 150. FIG. 2 is an enlarged cross-sectional view of an upper portion of the trace detection portal 100 further illustrating the calibration apparatus 150 of FIG. 1.

Referring to FIGS. 1 and 2, an embodiment of the trace detection portal 100 has two vertical sidewalls 112 and 114 that are spaced apart from each other at a distance "W" to form a sample collection chamber 116 through which a person may pass. The sidewalls 112 and 114 each have a length "L" that is sufficient to bracket the width or depth of a person standing in the center of the sample collection chamber 116. A ceiling 118, which is disposed at a height "H" above the floor or other surface that supports the trace detection portal 100, also forms part of the sample collection chamber 116. The height "H" of the ceiling 188 is sufficient to permit persons to pass easily into and through the sample collection chamber 116.

Additionally, the upper and lower portions of the trace detection portal 100 are defined by a horizontal axis (e.g., a horizontal plane) 105 that passes through a center point 106 of the trace detection portal 100. In an embodiment, the upper portion of the trace detection portal 100 is at or above the axis 105; and the lower portion of the trace detection portal 100 is at or below the axis 105. The upper portion of the sample collection chamber 116 gradually tapers from wide dimensions proximate the axis 105 to narrow dimensions proximate the sample collection port 120. In an embodiment, the sample collection port 120 is a hollow conduit extending from an interior upper surface of the sample collection chamber 116 into (and/or through) the ceiling 118 of the trace detection portal 100.

The sample collection port 120 collects and condenses the rising thermal plume of a person present within the sample collection chamber 116. A movable trap 122 provided within the smaller cross-sectional dimensions of the sample collection port 120 collects particles comprising a substance of interest that are entrained in the rising thermal plume. Non-limiting examples of articles comprising a substance of interest include particles, airborne trace chemicals in vapor form and skin flakes having adsorbed compounds thereon, among others.

A fan 124 provided at the upper portion of the sample collection port 120 rotates at a speed required to draw air in at about the same flow rate as the rising thermal plume. The suction provided by the fan 124 directs the thermal plume through the trap 122. A conveyor 126 provided on a substrate 102 moves the trap 122 into and out of a desorber 128, which is also provided on the substrate 102. The desorber 128 rapidly heats the inserted trap 122 to about 200 degrees Celsius to free the entrapped particles of interest. Contemporaneously, clean air injected into the desorber 128 is suctioned to draw the vaporized particles comprising a substance of interest into a detector 130, which detects and identifies the particles comprising a substance of interest.

In the embodiment shown in FIGS. 1 and 2, a calibration apparatus 150 is coupled with substrate 102, which has opposing first and second surfaces. A conveyor 126 and the desorber 128 may be disposed on the first surface of the substrate 102, and the detector 130 may be supported on the second surface of the substrate 102. A hollow conduit may link the desorber 128 to the detector 130. Particles comprising a substance of interest may be aspirated from the desorber 128, through the hollow conduit, and into the detector 130 for analysis.

An embodiment of the calibration apparatus 150 may comprise a calibrant container 160 that releasably contains a substance the detector 130 is configured to uniquely recognize as a calibrant. The calibration apparatus 150 may further comprise an actuator 170 coupled with a calibrant container 160 and a control means (e.g., controller) 180 configured to operate the actuator 170. In an embodiment, the actuator 170 may include an air pump 196, a first solenoid valve 185, a second solenoid valve 186, and/or conduits 181, 182, and 183. The actuator 170 may be configured to discharge a predetermined amount of calibrant into the trace detection portal's sample collection chamber 116 in response to a signal generated by the control means 180 and relayed to the actuator 170 via a wired or wireless communications link 190. A power source 195 provides electrical power to the control means 180, the first solenoid valve 185, the second solenoid valve 186, the air pump 196, the conveyor 126, the desorber 128, the detector 130, and/or other components of the trace detection portal 100. The power source 195 may be a generator, a battery, a photovoltaic cell, a hydrogen fuel cell, and the like.

In an embodiment, the conduit 181 connects the air pump 196 with the first solenoid valve 185. Additionally, the conduit 182 connects the first solenoid valve 185 with an inlet of a calibrant container 160. The conduit 183 connects an outlet of a calibrant container 160 with the second solenoid valve 186 and with the sample collection chamber 116, and the conduit 184 connects the first solenoid valve 185 with the desorber 128. Any suitable type of flexible or inflexible conduit may be used for each of conduit 181, 182, 183, and 184. Non-limiting examples of suitable conduit materials include metal, metal alloys, glass, plastic, polymers, and the like.

An end of the conduit 183 (or, alternatively, the outlet of the calibrant container) that connects with the sample collection chamber 116 may be suitably positioned at a predetermined distance from the trap 122 that permits the trap 122 to consistently collect all or a majority of the predetermined amount of calibrant that is released from the calibrant container 160 and infused into the sample collection chamber 116. The exact placement of the conduit 183 (or the outlet of the calibrant container 160) will vary depending on a number of factors, including, but not limited to: the size of the sample collection chamber 116, the configuration of the sample collection port 120, whether the sample collection chamber 116 is fully or partially enclosed, and the like.

The control means 180 is coupled with one or more components of the apparatus 150 described above. Non-limiting examples of the control means 180 include a computer subsystem 189, a computer input means 188, and a button, toggle, or slider switch 187, among others. The computer subsystem 189 may comprise a data bus that links a computer processor with a memory, a transceiver or modem, and the computer input means 188. The computer input means 188 may include, but is not limited to, a computer keyboard, a computer mouse, a computer touch screen, and the like.

In the embodiment illustratively shown in FIGS. 1 and 2, each of solenoid valves 185, 186 occupies a first default closed position, which prevents hot air from the air pump 196 from entering the inlet of a calibrant container 160 and prevents calibrant from reaching the sample collection chamber 116. Each of solenoid valves 185, 186 moves to a second open position in response to a signal generated by the control means 180.

When opened, the solenoid valves 185, 186 allow a predetermined amount of heated air and calibrant to infuse the sample collection chamber 116. Inside the sample collection chamber 116, at least the calibrant is drawn upwards into the sample collection port 120 by the fan 124. Particles comprising a substance of interest that forms the calibrant are captured and concentrated by the trap 122. Conveyor 126 inserts the trap 122 into the desorber 128, which rapidly heats the trap 122 to free the particles comprising the substance of interest. Clean air provided by the air pump 196 via conduit 181 and 184 is injected into the desorber 128. The clean air and the particles of interest freed from the trap 122 are then aspirated into the detector 130.

In an embodiment, the detector 130 is an ion mobility spectrometer ("IMS"), but other types of detectors known to a skilled artisan may also be used. (i.e., ion trap mobility spectrometer ("ITMS"), mass spectrometer, etc). Within an IMS detector 130, the particles comprising the substance of interest may be ionized (via a weak radioactive source or other means known to a skilled artisan) and caused to drift through a weak electric field. The time a particle takes to drift through the weak electric field is known as "time of flight." Experiments have shown that particle time of flight is a distinct "fingerprint" that enables the detector 130 to uniquely identify many different kinds of substances of interest.

In an embodiment, the substance of interest may be a calibrant releasably contained within the calibrant container 160. The calibrant may have a unique, predetermined "time of flight" different from the "times of flight" associated with other substances of interest, which may include, but are not limited to, explosives and narcotics, among others. In an embodiment, when an IMS detector 130 detects the "time of flight" uniquely associated with the calibrant, a calibration signal may be output to one or more components of the trace detection portal 100. The calibration signal may cause such components to automatically self-calibrate. One of these components may be an IMS detector 130, which may automatically self-calibrate using one or more peak values from (current) IMS spectra data.

Figure 3:
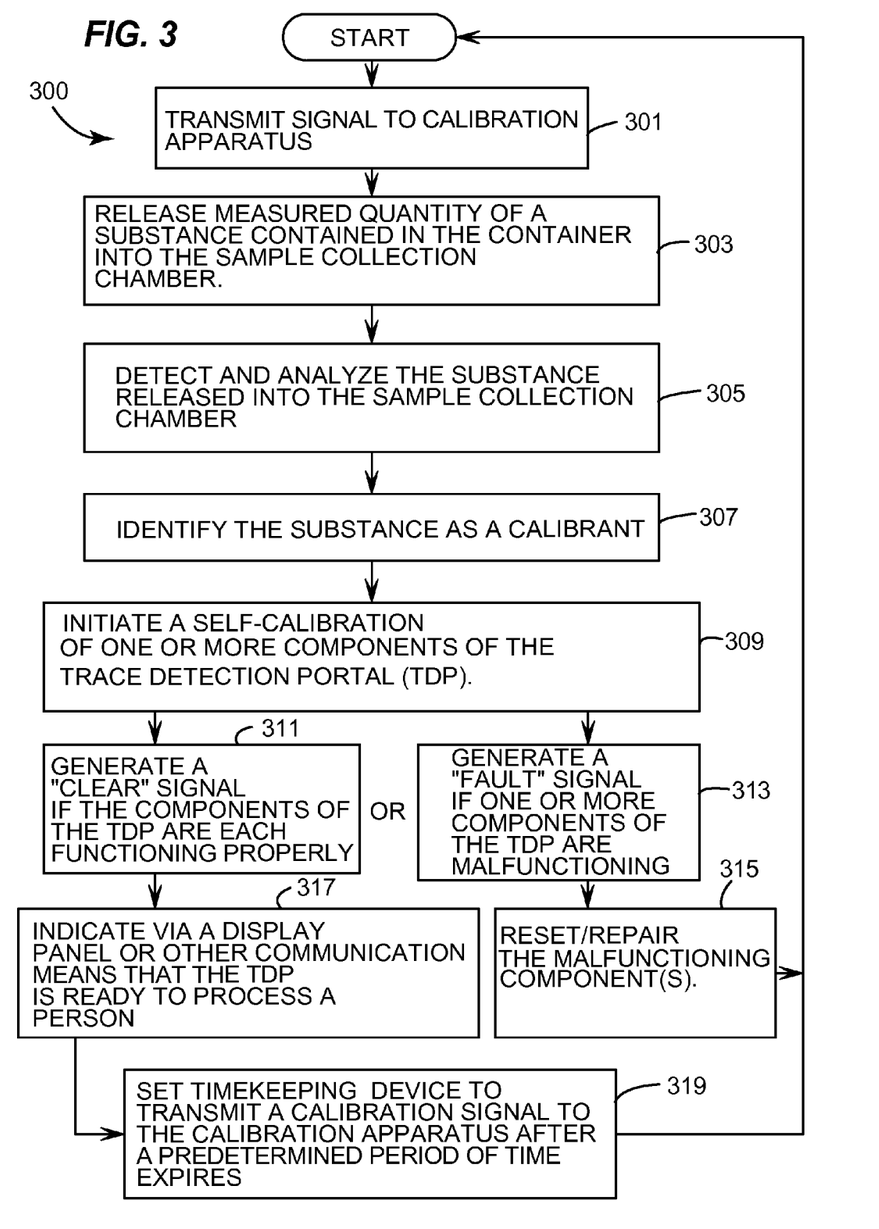
FIG. 3 is a flowchart illustrating an embodiment of a method of operating an embodiment of the calibration apparatus.

FIG. 3 is a flowchart illustrating an embodiment of a method 300 (hereinafter, "the method 300") of calibrating a trace detection portal 100. It will be appreciated that the method steps shown in FIG. 3 and described herein may be performed in any suitable order, and that variants of the method 300 may include one or more steps in addition to the ones herein shown and described.

Referring to FIGS. 1, 2, and 3, the method 300 is initiated by transmitting a signal from the control means 180 to the calibration apparatus 160 (block 301). As previously described, the control means 180 may generate and transmit this signal. The method 300 further comprises releasing a predetermined amount of a substance contained in a calibrant container 160 into the sample collection chamber 116 (block 303). As noted above, this step may be accomplished by opening both solenoid valves 185, 186. The method 300 further comprises analyzing the measured amount of substance released into the sample collection chamber 116 (block 305). As previously noted, this step may be accomplished using the detector 130 and/or a trap 122 located in the sample collection port 120. The method 300 yet further comprises identifying the measured amount of substance as a calibrant (block 307). As mentioned above, this step may be accomplished in an embodiment using ion mobility spectrometry (or other suitable detection method known to a skilled artisan), and/or by comparing the analysis data with the data on the above-referenced threat and/or calibrant lists. The method 300 further comprises automatically initiating a self-calibration of one or more components of the trace detection portal in response to the identification of the substance as a calibrant (block 309). As described above, this step may further include outputting a calibration signal to one or more components of the trace detection portal 100. One such component may be the detector 130.

The method 300 further comprises generating a "clear" signal if the components of the trace detection portal 100 are each functioning properly (block 311). Alternatively, the method 300 further comprises generating a "fault" signal if one or more components of the trace detection portal 100 are malfunctioning (block 313). If the "clear" signal has been generated, the method 300 further comprises indicating via a display panel, or other communication means, that the trace detection portal 100 is ready to process persons (block 317). If the "fault" signal has been generated, the method 300 further comprises resetting and/or repairing the malfunctioning component(s) (block 315). Following the reset and/or repair, the method 300 may loop back to the step of transmitting a signal to the calibration apparatus 150 (block 301) and proceed as described above. If the trace detection portal 100 has been indicated to be ready to process a person, the method 300 may optionally comprise the step of setting a timekeeping device to transmit the signal to the calibration apparatus after the expiration of a predetermined period of time (block 319). After the timekeeping device is set, the method 300 may loop back to the step of transmitting the signal to the calibration apparatus (block 301). Alternatively, the method 300 may end after performing the steps represented by either (block 317) or (block 319).

Figure 4:
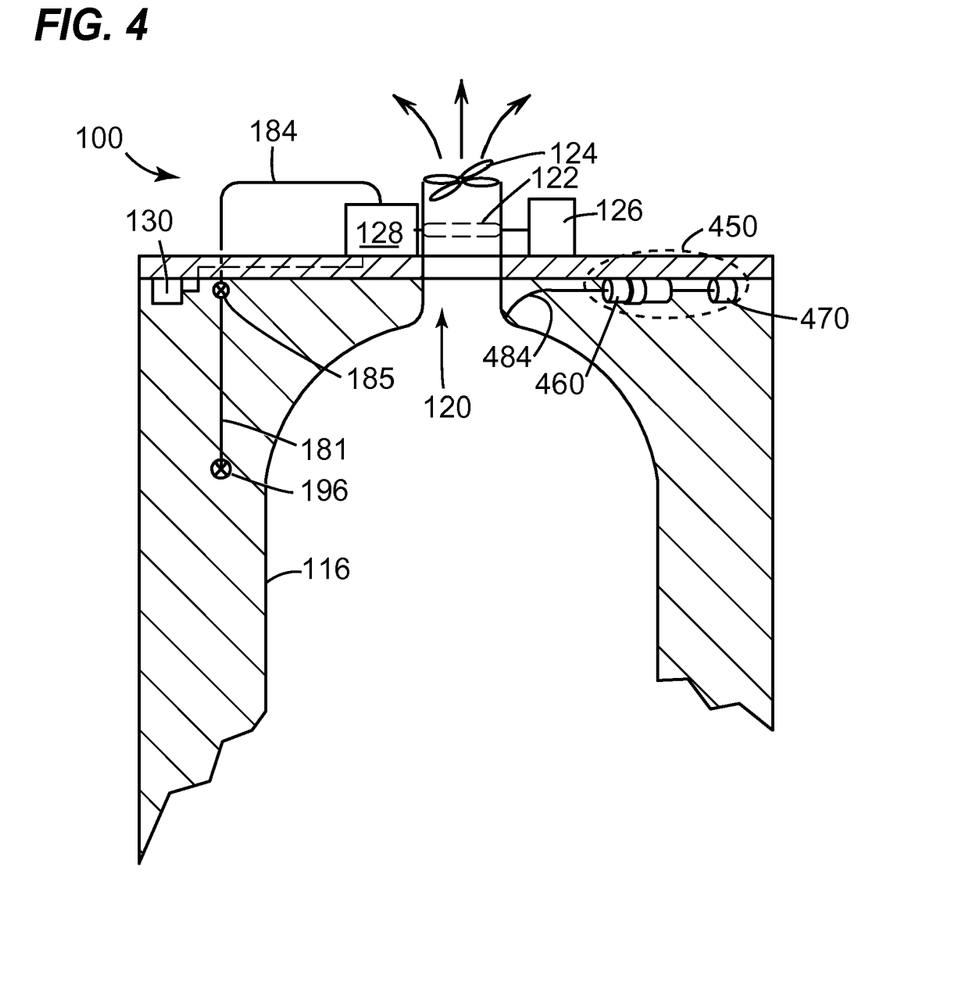
FIG. 4 is another cross-sectional view of the upper portion of the trace detection portal of FIG. 1 more clearly depicting another embodiment of the calibration apparatus.

FIG. 4 is a cross-sectional diagram of an upper portion of the trace detection portal 100 illustrating another embodiment of a calibration apparatus 450 in which a calibrant container 460 containing a calibrant in an initial liquid, vapor, or aerosol state is insulated from receiving heat generated by the desorber 128. The heating effects of the desorber 128 may be minimized or eliminated by locating the calibration apparatus 450 away from the desorber 128, as illustratively shown in FIG. 4.

In an embodiment where the calibration apparatus 450 is positioned near the desorber 128, insulation may be provided by an insulator disposed between the calibration apparatus and the desorber 128. The insulator may be air disposed between the calibrant container 460 and the substrate 102 and/or the desorber 128. Alternatively, the insulator may be any suitable material having heat-insulative properties. Non-limiting examples of suitable insulator materials include fiberglass, foam, ceramic fibers, microporous insulation, high temperature cloth, insulative laminates, insulative woven tapes, high temperature paper/felt (e.g., a blend of fibers, binders, and additives that can resist or contain heat), and the like. Additionally (or alternatively), a calibrant container 460 may be formed of plastic or another material having heat-insulative properties.

Referring to FIGS. 1, 2, and 4, the calibration apparatus 450 also includes an actuator 470. In an embodiment, the actuator 470 is a plunger/piston that is directly coupled with an inlet of a calibrant container 460. The actuator 470 may also be coupled with the control means 180 via wired or wireless communication link 190, and optionally with the power source 195. In response to a signal received from the control means 180, the actuator 470 operates to discharge a predetermined amount of calibrant into the sample collection chamber 116 for collection by the trap 122 and analysis by the detector 130.

In an embodiment, the control means 180 may be configured to initiate and execute a calibration of the trace detection portal upon receipt of a signal from a timekeeping device. The timekeeping device may be configured to automatically transmit the signal to the calibration apparatus upon expiration of a predetermined period-of-time.

Referring to FIGS. 1, 2, and 4, each of a calibrant containers 160, 460 are formed of metal, plastic, or other suitable material, and are either single-use, disposable, or rechargeable. The phrase "single-use container" refers to a calibrant container 160,460, the contents of which are designed to last the operational lifetime of the trace detection portal 100 in which it is used without replacement. The phrase "disposable container" refers to a calibrant container 160,460 designed to be thrown away after being emptied of its contents. The phrase "rechargeable container" refers to a calibrant container 160,460 designed to be refilled with a calibrant after being emptied of its contents. In an embodiment, a single-use container may be fixedly attached to the substrate 102. In another embodiment, either a disposable container or a rechargeable container may be detachably coupled with the substrate 102.

Figure 5:
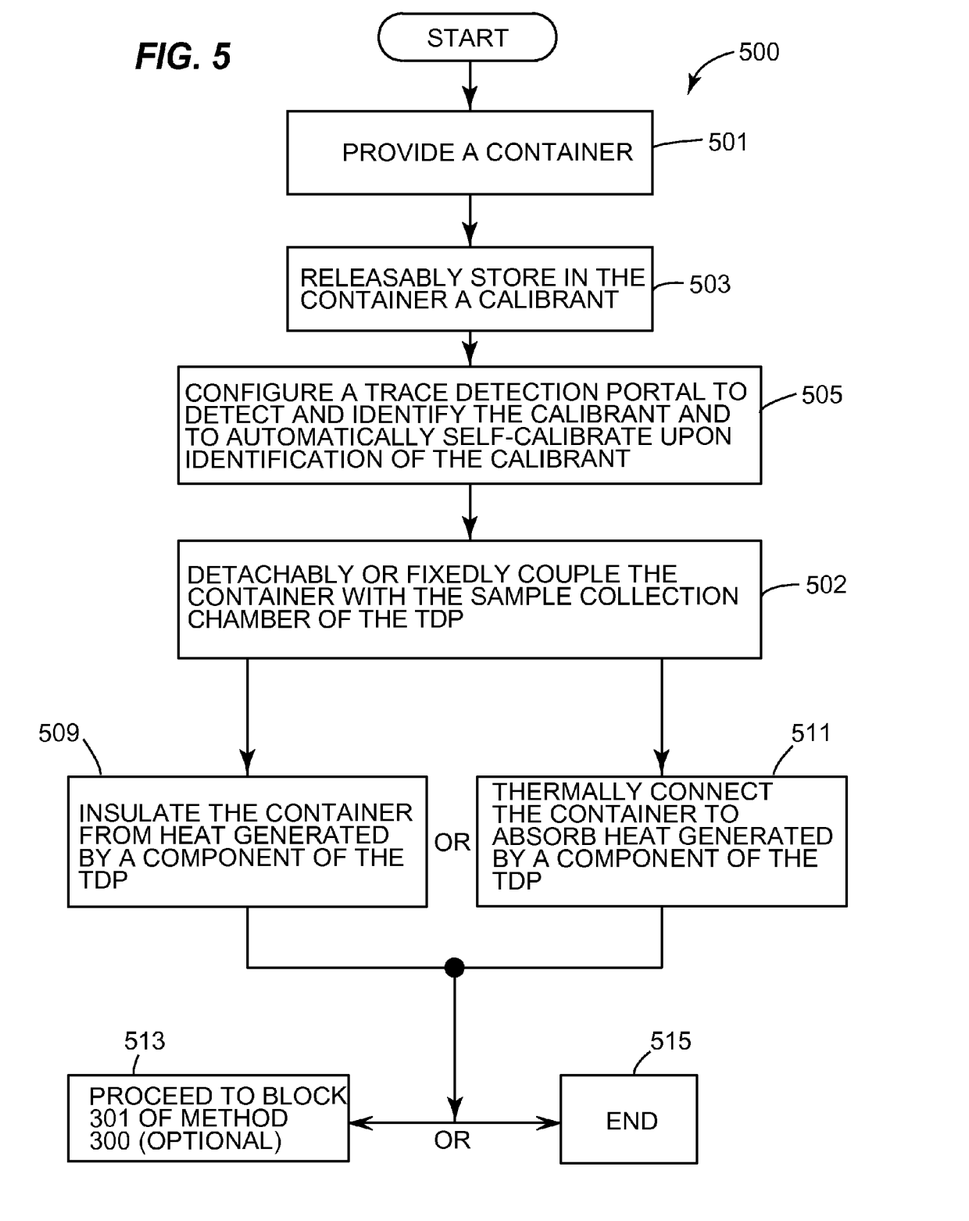
FIG. 5 is another flowchart illustrating an embodiment of a method of fitting or retrofitting an embodiment of the calibration apparatus to a newly manufactured or existing trace detection portal.

FIG. 5 is another flowchart illustrating an embodiment of a method 500 (hereinafter, "the method 500") of fitting or retrofitting to a trace detection portal 100 an embodiment of the claimed calibration apparatus 150,450 shown in FIGS. 1, 2, and 4. It will be appreciated that the method steps shown in FIG. 5 and described herein may be performed in any suitable order, and that variants of the method 500 may include one or more steps in addition to the ones herein shown and described.

Referring to FIGS. 1, 2, 4, and 5, a first step of the method 500 may be providing a calibrant container 160,460 (block 501). The method 500 may further comprise releasably storing a calibrant within the calibrant container 160,460 (block 503). The method 500 may further comprise configuring a trace detection portal 100 to detect and identify a calibrant and to automatically self-calibrate upon identification of the calibrant (block 505). The method 500 may further comprise detachably or fixedly coupling the calibrant container 160, 460 with the sample collection chamber 116 of the trace detection portal 100 (block 507). The method 500 may further comprise insulating a calibrant container 160,460 from heat generated by a component of the trace detection portal 100 (block 509). Alternatively, the method 500 may further comprise thermally connecting a calibrant container 160,460 to absorb heat generated by a component of the trace detection portal 100 (block 511). After performing either the step represented by block 509 or by block 511, the method 500 may end (block 515) or may optionally perform the steps represented by blocks 301, 303, 305, 307, 309, 311, 313, 315, 317, and 319 of method 300, as shown in FIG. 3 and described above.

Figure 6:
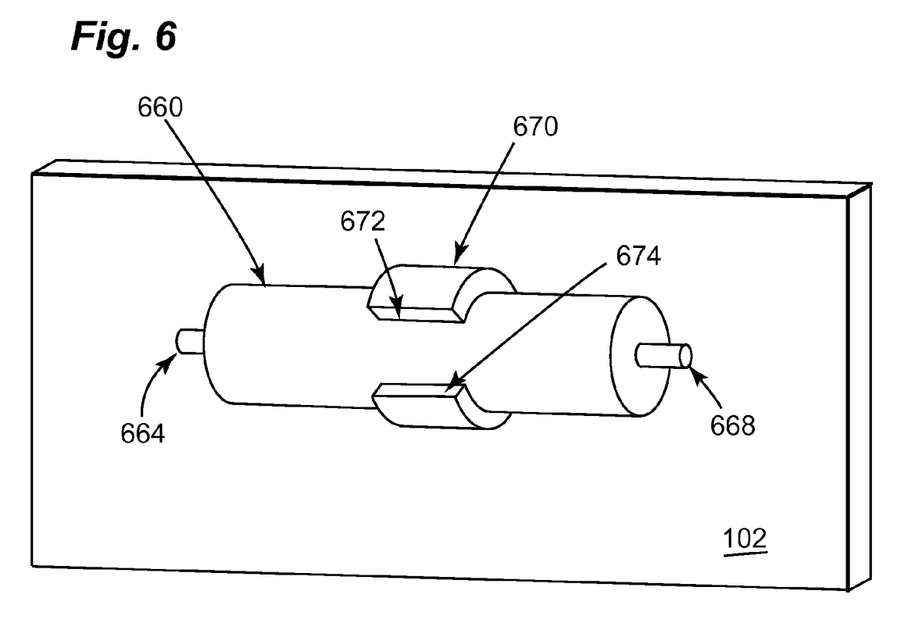
FIG. 6 is a perspective view of an embodiment of a calibrant container and an embodiment of a bracket used to detachably or fixedly couple the calibrant container to a component of the trace detection portal of FIG. 1.

FIG. 6 is a diagram illustrating a quick-release bracket 670 that may be used to detachably couple a calibrant container 660 with a substrate 102 of a trace detection portal. Referring to FIGS. 1, 2, 4, and 6, during manufacture of a new trace detection portal 100, for example, the bracket 670 may be integrally formed as part of the substrate 102 or formed separately from the substrate 102 and attached thereto using a fastener. Similarly, in an embodiment of the invention directed to retrofitting a previously manufactured trace detection portal 100, the bracket 670 may be attached to the substrate 102 using a fastener. Non-limiting examples of fasteners include: clips, screws, bolts, nails, adhesives, and the like.

In FIG. 6, the bracket 670 is illustratively depicted as a quick-release bracket that has a "c" shape with opposing ends 672,674 separated by a gap. The quick-release bracket 670 and a calibrant container 660 may take any suitable shape and/or configuration, and are not limited to those illustratively depicted in FIG. 6. For example, the bracket 670 may comprise a first strip of hook-and-loop material adhered to the substrate 102 and a second opposing strip of hook-and-loop material adhered to an exterior portion of a calibrant container 660. In another embodiment, the bracket 670 may comprise a half-cylinder or a four-sided box attached to the substrate 102, and into which a calibrant container 660 removably fits. It will be appreciated, however, that other variants of the bracket 670 and a calibrant container 660 are possible.

As shown in FIG. 6, an embodiment of a calibrant container 660 having a generally cylindrical shape with an inlet 662 and an outlet 664 formed at opposing ends thereof is gripped by the bracket 670. A calibrant container 660 may be inserted within the bracket 670 by positioning a calibrant container 660 adjacent the gap between the opposing ends 672,674 of the bracket 670 and compressing a calibrant container 660 until the opposing ends 672,674 spread apart and allow a calibrant container 660 to enter the interior of the bracket 670. A calibrant container 660 may be detached from the bracket 670 by pulling a calibrant container 670 towards the gap between the opposing ends 672,674 of the bracket 670 until the opposing ends 672,674 spread apart and allow a calibrant container 660 to exit the bracket 670.

Embodiments of the invention illustrated in the appended drawings and illustratively described above position a detector 130, a sample collection port 120 coupled with the detector, and a calibration apparatus 150 in an upper portion of a trace detection portal 100. In an embodiment, the upper portion of a trace detection portal includes regions of the trace detection portal that are at or above a horizontal plane (e.g., a plane that substantially parallels the floor or support surface on which the trace detection portal is placed) that passes through a center point of the trace detection portal. Alternative embodiments of the invention, however, position the detector 130 (and/or a sample collection port 120 coupled with the detector 130) and/or the calibration apparatus 150 in a lower portion of the trace detection portal 100. In an embodiment, the lower portion of the trace detection portal 100 includes regions that are at or below the horizontal plane that passes through the center point of the trace detection portal. In such alternative embodiments, for example, the detector 130, a sample collection port 120 coupled with the detector 130, and/or the calibration apparatus 150 may each be located in the floor or lower sidewalls of the trace detection portal 100.

A detailed description of various embodiments of the invention has been provided; however, modifications within the scope of the invention will be apparent to persons having ordinary skill in the above-referenced technological field. Such persons will appreciate that features described with respect to one embodiment may be applied to other embodiments. Thus, the scope of the invention is to be properly construed with reference to the following claims.

What is claimed is:

1. A method for self-calibrating one or more components of a trace detection portal that includes a sample collection chamber, the method comprising:
   receiving a signal from a controller coupled with the trace detection portal;
   releasing a predetermined amount of a substance from a calibrant container into the sample collection chamber in response to the signal received from the controller;
   detecting and analyzing the substance;
   identifying the substance as a calibrant; and
   automatically initiating a self-calibration of one or more components of the trace detection portal in response to the identification of the calibrant.

2. The method of claim 1, further comprising:
   generating a "clear" signal if the one or more components are each functioning properly; and
   indicating via a display panel or other communication means that the trace detection portal is ready to process a person.

3. The method of claim 2, further comprising:
   setting a timekeeping device to transmit the signal to the calibration apparatus after an expiration of a predetermined period of time.

4. The method of claim 1, further comprising:
   generating a "fault" signal if one of the one or more components is malfunctioning; and
   at least one of resetting the malfunctioning component(s) and repairing the malfunctioning component(s).

5. A method, comprising:
   configuring a trace detection portal to detect and uniquely identify a calibrant and to automatically self-calibrate one or more components of the trace detection portal upon the identification of the calibrant from particles of interest collected from within a sample collection chamber of the trace detection portal; and
   coupling an outlet of a calibrant container with the sample collection chamber.

6. The method of claim 5, wherein the step of coupling an outlet of the calibrant container with the sample collection chamber comprises one of:
   detachably coupling the outlet of the calibrant container with the sample collection chamber, and
   fixedly coupling the outlet of the calibrant container with the sample collection chamber.

7. The method of claim 5, further comprising:
   insulating the calibrant container from heat generated by one of the one or more components of the trace detection portal.

8. The method of claim 5, further comprising:
   thermally connecting the calibrant container to absorb heat generated by one of the one or more components of the trace detection portal.

9. A method for calibrating a trace detection portal, the method comprising:
   providing a calibrant container having an outlet; and
   releasably storing a calibrant within the calibrant container, wherein the calibrant is a substance the trace detection portal is configured to detect and uniquely identity as a calibrant, and which causes one or more components of the trace detection portal to self-calibrate.

* * * * *